(12) United States Patent
Sabilla

(10) Patent No.: US 9,615,897 B2
(45) Date of Patent: Apr. 11, 2017

(54) SELF-LIGATING ORTHODONTIC BRACKET

(75) Inventor: Jefferson Sabilla, Ontario, CA (US)

(73) Assignee: Ormco Corporation, Orange, CA (US)

( * ) Notice: Subject to any disclaimer, the term of this patent is extended or adjusted under 35 U.S.C. 154(b) by 0 days.

(21) Appl. No.: 13/224,908

(22) Filed: Sep. 2, 2011

(65) Prior Publication Data

US 2012/0064476 A1 Mar. 15, 2012

Related U.S. Application Data

(60) Provisional application No. 61/381,868, filed on Sep. 10, 2010.

(51) Int. Cl.
*A61C 3/00* (2006.01)
*A61C 7/28* (2006.01)

(52) U.S. Cl.
CPC ............... *A61C 7/28* (2013.01); *A61C 7/285* (2013.01)

(58) Field of Classification Search
CPC ...... A61C 2201/007; A61C 7/30; A61C 7/285
USPC ...... 433/8, 9, 10, 11, 2, 12, 13, 14
See application file for complete search history.

(56) References Cited

U.S. PATENT DOCUMENTS

| | | |
|---|---|---|
| 3,748,740 A | 7/1973 | Wildman |
| 4,077,126 A | 3/1978 | Pletcher |
| 4,103,423 A | 8/1978 | Kessel |
| 4,149,314 A | 4/1979 | Nonnenmann |
| 4,337,037 A | 6/1982 | Kurz |
| 4,371,337 A | 2/1983 | Pletcher |
| 4,419,078 A | 12/1983 | Pletcher |
| 4,443,189 A | 4/1984 | Wildman |
| 4,496,317 A | 1/1985 | Hulsey |
| 4,559,012 A | 12/1985 | Pletcher |
| 4,575,337 A | 3/1986 | Fujita |
| 4,634,662 A | 1/1987 | Rosenberg |

(Continued)

FOREIGN PATENT DOCUMENTS

| | | |
|---|---|---|
| CN | 1826087 A | 8/2006 |
| CN | 201453387 U | 5/2010 |

(Continued)

OTHER PUBLICATIONS

Herve Chabus; European Search Report issued in related European Patent Application No. EP 11 18 0388; Nov. 29, 2011; 4 pages; European Patent Office.

(Continued)

*Primary Examiner* — Cris L Rodriguez
*Assistant Examiner* — Mirayda A Aponte
(74) *Attorney, Agent, or Firm* — Wood Herron & Evans LLP

(57) ABSTRACT

An orthodontic bracket for coupling an archwire with a tooth includes a bracket body, a hinge pin, and a latch. The bracket body includes a first surface configured to be mounted to the tooth and an archwire slot in a second surface. The hinge pin includes a first shaft portion coupled with the bracket body. The latch is coupled to the bracket body by a second shaft portion of the hinge pin. The latch is movable between an opened position and a closed position. A cross-sectional profile of the first shaft portion and/or the second shaft portion of the hinge pin is configured to elastically deform to impart a spring bias to the latch that opposes movement of the latch relative to the bracket body.

30 Claims, 9 Drawing Sheets

(56) References Cited

U.S. PATENT DOCUMENTS

| | | |
|---|---|---|
| 4,655,708 A | 4/1987 | Fujita |
| 4,669,981 A | 6/1987 | Kurz |
| 4,698,017 A | 10/1987 | Hanson |
| 4,712,999 A | 12/1987 | Rosenberg |
| 4,786,252 A | 11/1988 | Fujita |
| 5,224,858 A | 7/1993 | Hanson |
| 5,474,445 A | 12/1995 | Voudouris |
| 5,474,446 A | 12/1995 | Wildman et al. |
| 5,511,976 A | 4/1996 | Wildman |
| 5,516,284 A | 5/1996 | Wildman |
| 5,685,711 A | 11/1997 | Hanson |
| 5,700,145 A | 12/1997 | Wildman |
| 5,711,666 A | 1/1998 | Hanson |
| 5,738,513 A | 4/1998 | Hermann |
| 5,791,897 A | 8/1998 | Wildman |
| 5,857,849 A | 1/1999 | Kurz |
| 5,857,850 A | 1/1999 | Voudouris |
| 5,863,199 A | 1/1999 | Wildman |
| 5,863,360 A | 1/1999 | Wood et al. |
| 5,908,293 A * | 6/1999 | Voudouris ................. 433/10 |
| 5,913,680 A | 6/1999 | Voudouris |
| 5,931,667 A | 8/1999 | Papandreas |
| 6,042,373 A | 3/2000 | Hermann |
| 6,071,119 A | 6/2000 | Christoff et al. |
| 6,168,428 B1 | 1/2001 | Voudouris |
| 6,247,923 B1 | 6/2001 | Vashi |
| 6,257,883 B1 | 7/2001 | Voudouris |
| 6,264,468 B1 | 7/2001 | Takemoto |
| 6,325,622 B1 | 12/2001 | Kelly et al. |
| 6,347,939 B2 | 2/2002 | Abels |
| 6,506,049 B2 | 1/2003 | Hanson |
| 6,554,612 B2 | 4/2003 | Georgakis et al. |
| 6,616,445 B2 | 9/2003 | Abels et al. |
| 6,655,957 B2 | 12/2003 | Abels et al. |
| 6,655,958 B2 | 12/2003 | Abels et al. |
| 6,659,766 B2 | 12/2003 | Abels et al. |
| 6,659,767 B2 | 12/2003 | Abels et al. |
| 6,695,612 B2 | 2/2004 | Abels et al. |
| 6,726,474 B2 | 4/2004 | Spencer |
| 6,776,613 B2 | 8/2004 | Orikasa |
| 6,932,597 B2 | 8/2005 | Abels et al. |
| 6,939,133 B2 | 9/2005 | Voudouris |
| 6,942,483 B2 | 9/2005 | Heiser |
| 6,960,080 B2 | 11/2005 | Abels et al. |
| 6,960,081 B2 | 11/2005 | Abels et al. |
| 6,964,565 B2 | 11/2005 | Abels et al. |
| 7,025,591 B1 | 4/2006 | Kesling |
| 7,063,529 B2 | 6/2006 | Abels et al. |
| 7,063,530 B2 | 6/2006 | Abels et al. |
| 7,104,791 B2 * | 9/2006 | Hanson ................. A61C 7/145 433/10 |
| 7,204,690 B2 | 4/2007 | Hanson |
| 7,234,935 B2 | 6/2007 | Abels et al. |
| 7,247,019 B2 | 7/2007 | Abels et al. |
| 7,249,397 B2 | 7/2007 | Abels et al. |
| 7,396,230 B2 | 7/2008 | Abels et al. |
| 7,416,408 B2 | 8/2008 | Farzin-Nia et al. |
| 7,611,352 B2 | 11/2009 | Abels et al. |
| 7,674,110 B2 | 3/2010 | Oda |
| 7,695,277 B1 | 4/2010 | Stevens |
| 2002/0034715 A1 | 3/2002 | Hanson |
| 2002/0110776 A1 | 8/2002 | Abels et al. |
| 2004/0166458 A1 | 8/2004 | Opin et al. |
| 2005/0019719 A1 | 1/2005 | Hanson |
| 2005/0186525 A1 | 8/2005 | Abels et al. |
| 2006/0084025 A1 | 4/2006 | Abels et al. |
| 2006/0263736 A1* | 11/2006 | Moon ................. 433/9 |
| 2007/0224569 A1* | 9/2007 | Oda ................. A61C 7/02 433/10 |
| 2007/0243497 A1 | 10/2007 | Voudouris |
| 2007/0259304 A1 | 11/2007 | Hagelganz et al. |
| 2008/0131831 A1 | 6/2008 | Abels et al. |
| 2008/0213718 A1 | 9/2008 | Abels et al. |
| 2008/0241782 A1 | 10/2008 | Abels et al. |
| 2009/0004619 A1 | 1/2009 | Oda et al. |
| 2009/0162807 A1 | 6/2009 | Hagelganz et al. |
| 2009/0170049 A1 | 7/2009 | Heiser |
| 2009/0325118 A1 | 12/2009 | Lewis et al. |
| 2009/0325120 A1 | 12/2009 | Lewis et al. |
| 2010/0159411 A1 | 6/2010 | Oda |
| 2010/0178629 A1 | 7/2010 | Oda et al. |

FOREIGN PATENT DOCUMENTS

| | | |
|---|---|---|
| EP | 1 836 990 | 9/2007 |
| JP | 3129689 B2 | 1/2001 |
| JP | 2001503305 A | 3/2001 |
| JP | 2006528007 A | 12/2006 |
| JP | 2007252926 A | 10/2007 |
| JP | 2010531717 A | 9/2010 |

OTHER PUBLICATIONS

The State Intellectual Property Office of the People's Republic of China, Official Action issued in Application No. 201110323950.4 dated May 6, 2015.

Japan Patent Office, Official Action issued in Japanese Patent Application No. 2011-196878 dated Aug. 17, 2015.

China Patent & Trademark Office, Official Action issued in Application No. 201110323950.4 dated Dec. 16, 2015.

Chinese Patent Office: Office Action issued in Chinese Patent Application No. 201110323950.4 mailed Jun. 27, 2016, 5 pages.

* cited by examiner

SELF-LIGATING ORTHODONTIC BRACKET

CROSS REFERENCE TO RELATED CASES

This application claims priority to U.S. Provisional Patent Application Ser. No. 61/381,868 filed Sep. 10, 2010, the disclosure of which is incorporated by reference herein in its entirety.

TECHNICAL FIELD

The invention relates generally to orthodontic brackets and, more particularly, to self-ligating orthodontic brackets having movable closure members such as clips or latches.

BACKGROUND

Orthodontic brackets represent a principal component of all corrective orthodontic treatments devoted to improving a patient's occlusion. In conventional orthodontic treatments, an orthodontist or an assistant affixes brackets to the patient's teeth and engages an archwire into a slot of each bracket. The archwire applies corrective forces that coerce the teeth to move into correct positions. Traditional ligatures, such as small elastomeric O-rings or fine metal wires, are employed to retain the archwire within each bracket slot. Due to difficulties encountered in applying an individual ligature to each bracket, self-ligating orthodontic brackets have been developed that eliminate the need for ligatures by relying on a movable portion or member, such as a latch or slide, for retaining the archwire within the bracket slot.

While self-ligating brackets have been generally successful, manufacturers of such brackets continually strive to improve the aesthetics associated with self-ligating brackets, the use and functionality of self-ligating brackets, and the costs and manufacturability of self-ligating brackets.

SUMMARY OF THE INVENTION

In one embodiment, an orthodontic bracket for coupling an archwire with a tooth is provided. The orthodontic bracket comprises a bracket body, a resilient hinge pin, and a latch. The bracket body includes a first surface configured to be mounted to the tooth, a second surface, and an archwire slot in the second surface. The hinge pin includes a first shaft portion operatively coupled with the bracket body and a second shaft portion. The latch is operatively coupled to the bracket body by the second shaft portion of the hinge pin for movement about an axis of rotation defined by the hinge pin. The latch is movable between an opened position in which the archwire is insertable into the archwire slot and a closed position in which the latch retains the archwire in the archwire slot. A cross-sectional profile of the first shaft portion and/or the second shaft portion of the hinge pin is configured to elastically deform to impart a spring bias to the latch.

The cross-section of the first shaft portion and/or the second shaft portion may change depending on the position of the latch relative to the bracket body and/or the direction of any forces on the latch. In one embodiment, one of the first shaft portion and the second shaft portion of the hinge pin is configured to elastically deform from a first cross-sectional profile when the latch is in the closed position to a second cross-sectional profile when the latch is moved from the closed position, the spring bias opposing movement of the latch from the closed position, and the first cross-sectional profile and the second cross-sectional profile being different.

In one embodiment, one of the first shaft portion and the second shaft portion of the hinge pin is configured to elastically deform from the second cross-sectional profile to a third cross-sectional profile when the latch is rotated toward the opened position.

In one embodiment, the hinge pin is a hollow cylinder.

In one embodiment, the bracket body includes a bore for receiving the first shaft portion and the latch includes an aperture for receiving the second shaft portion and at least one of the aperture and the bore have a non-symmetric cross-sectional profile along a plane that includes the axis of rotation.

In one embodiment, the bore includes a bore cross-sectional profile and the aperture includes an aperture cross-sectional profile. One of the bore cross-sectional profile and the aperture cross-sectional profile is substantially non-congruent relative to the corresponding cross-sectional profile of the first shaft portion or second shaft portion. The hinge pin is configured to move relative to the bore or the aperture and elastically deform toward at least a portion of the substantially non-congruent cross-sectional profile when the latch is moved from the closed position.

In one embodiment, the aperture cross-sectional profile is substantially non-congruent relative to the second shaft portion and includes a central portion and a first narrowed end. The second shaft portion is located in the central portion when the latch is in the closed position and elastically deforms into the first narrowed end when the latch is moved from the closed position.

In one embodiment, the central portion of the aperture cross-sectional profile is sized to elastically deform the hinge pin in the closed position.

In one embodiment, the substantially non-congruent cross-sectional profile includes a first narrowed end contiguous with the central portion. One of the first shaft portion and the second shaft portion is located in the central portion when the latch is in the closed position and elastically deforms into the first narrowed end when the latch is moved from the closed position.

In one embodiment, the non-congruent cross-sectional profile includes a second narrowed end contiguous with the central portion, and one of the first shaft portion and the second shaft portion elastically deforms into the second narrowed end when the latch is moved.

In one embodiment, the latch includes an outer periphery including a cam surface configured to contact the bracket body and move the latch in a non-collinear direction relative to the axis of rotation when the latch is rotated about the axis of rotation from the closed position to the opened position.

In one embodiment, the cam surface is configured to contact the bracket body to hold the latch in the opened position.

In one embodiment, the bracket body includes a recess and the latch includes a projection engaged with the recess when the latch is in the closed position, so as to inhibit movement of the latch about the axis of rotation from the closed position toward the opened position. The spring bias of the hinge pin opposes movement of the latch in a direction away from the recess.

In one embodiment, the bracket body includes a shoulder engaged with the latch when the latch is in the closed position, so as to inhibit movement of the latch about the axis of rotation from the closed position toward the opened position. The spring bias of the hinge pin opposes movement of the latch away from the shoulder.

In one embodiment, the latch is configured to contact the bracket body when the latch is in the opened position and is moved toward the closed position, so as to inhibit movement of the latch to the closed position.

BRIEF DESCRIPTION OF THE DRAWINGS

The accompanying drawings, which are incorporated in and constitute a part of this specification, illustrate embodiments of the invention and, together with the detailed description given below, serve to explain the invention.

DETAILED DESCRIPTION

Figure 1:
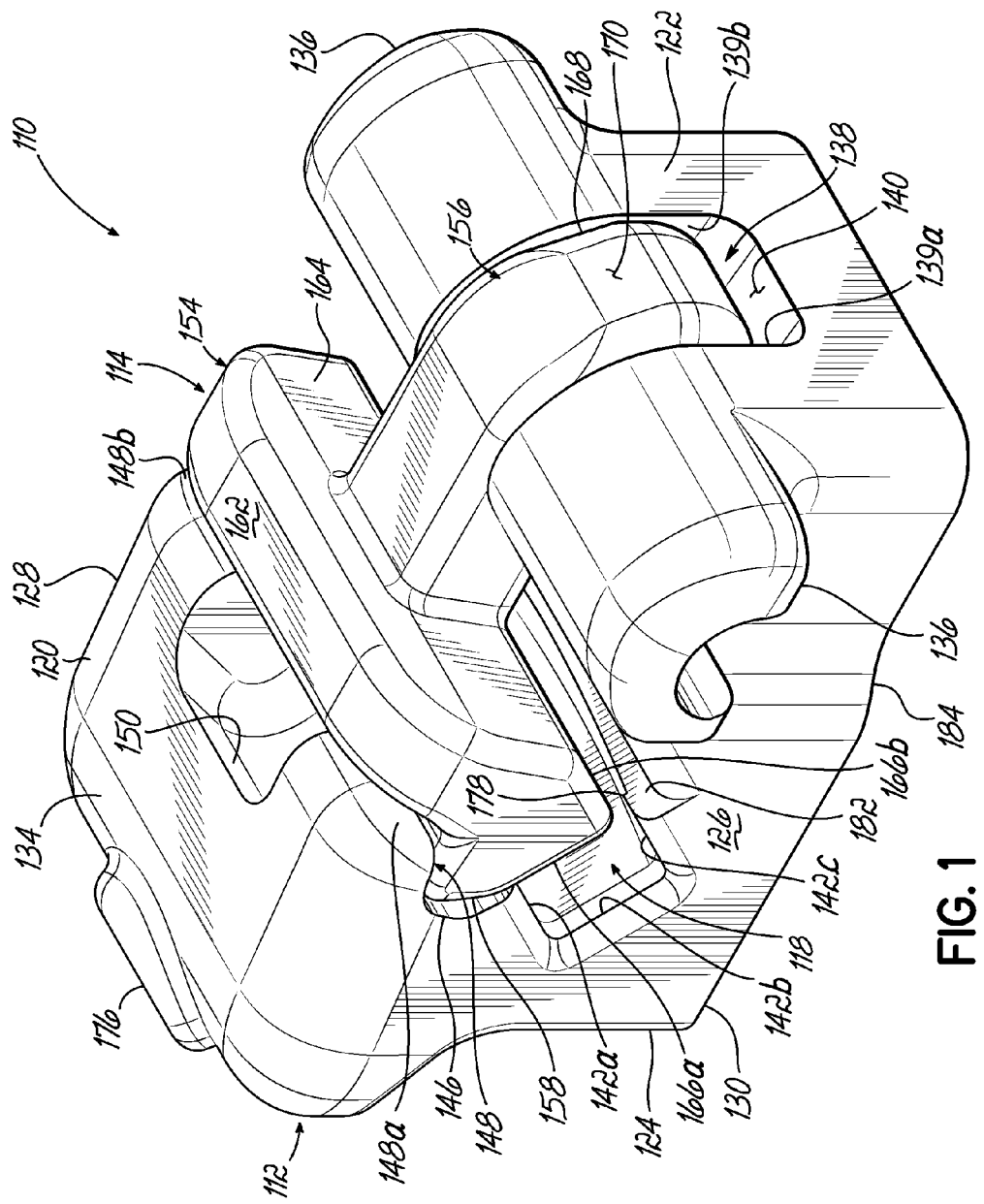
FIG. 1 is a perspective view of a self-ligating orthodontic bracket in accordance with one embodiment of the invention, with a ligating latch shown in an closed position.
Figure 2:
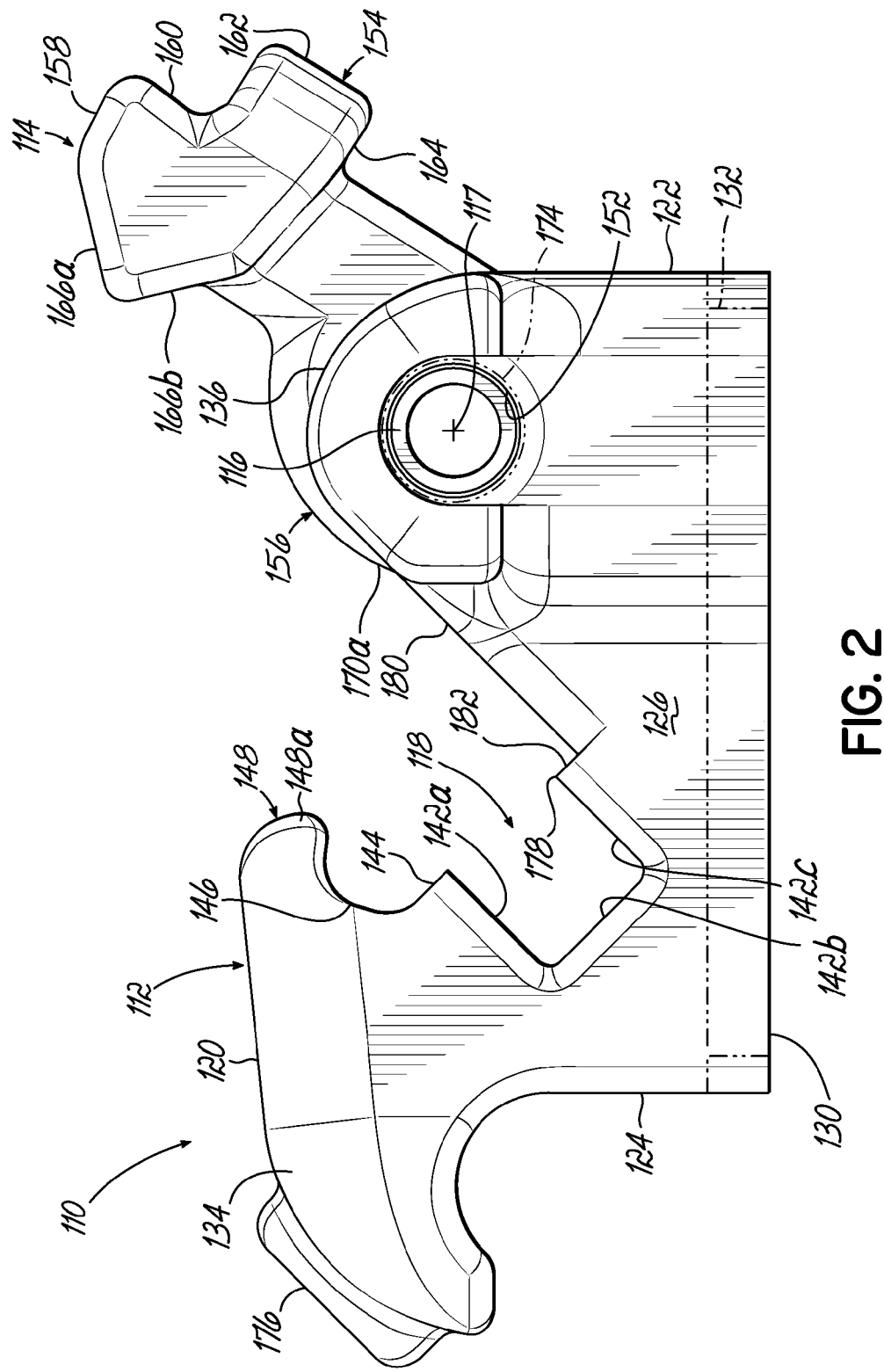
FIG. 2 is a side elevation view of the self-ligating orthodontic bracket shown in FIG. 1 with the ligating latch shown in an opened position.
Figure 3:
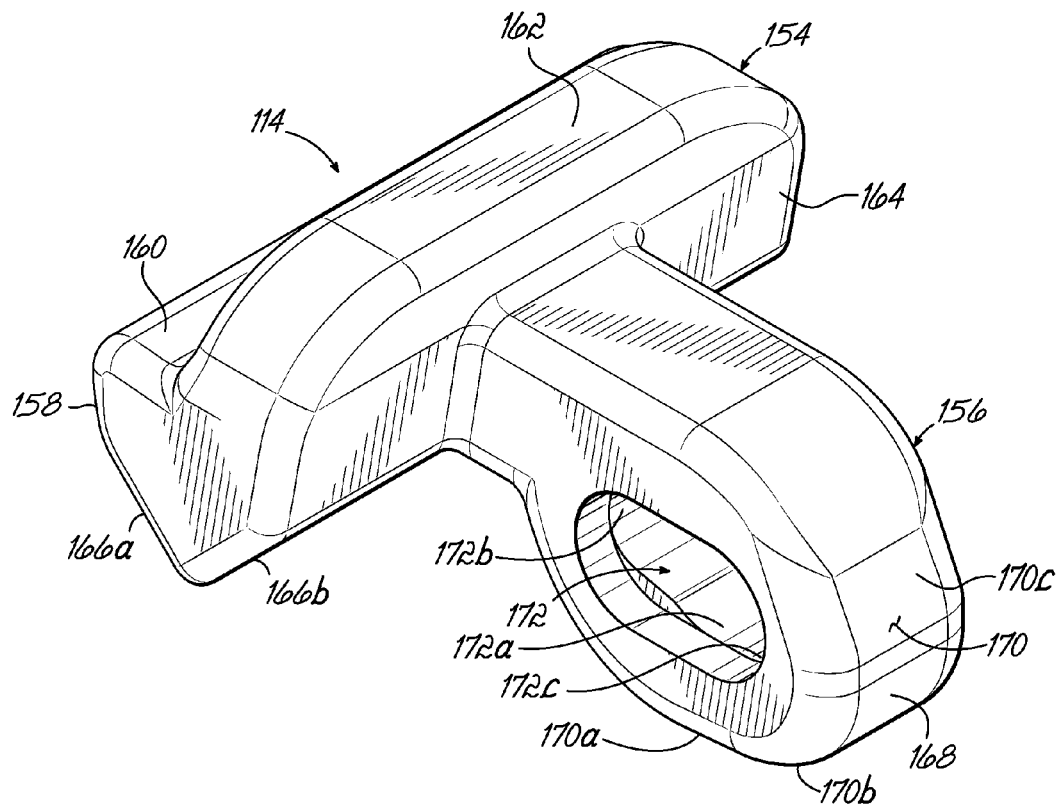
FIG. 3 is a perspective view of the ligating latch of the self-ligating orthodontic bracket shown in FIG. 1.
Figure 3A:
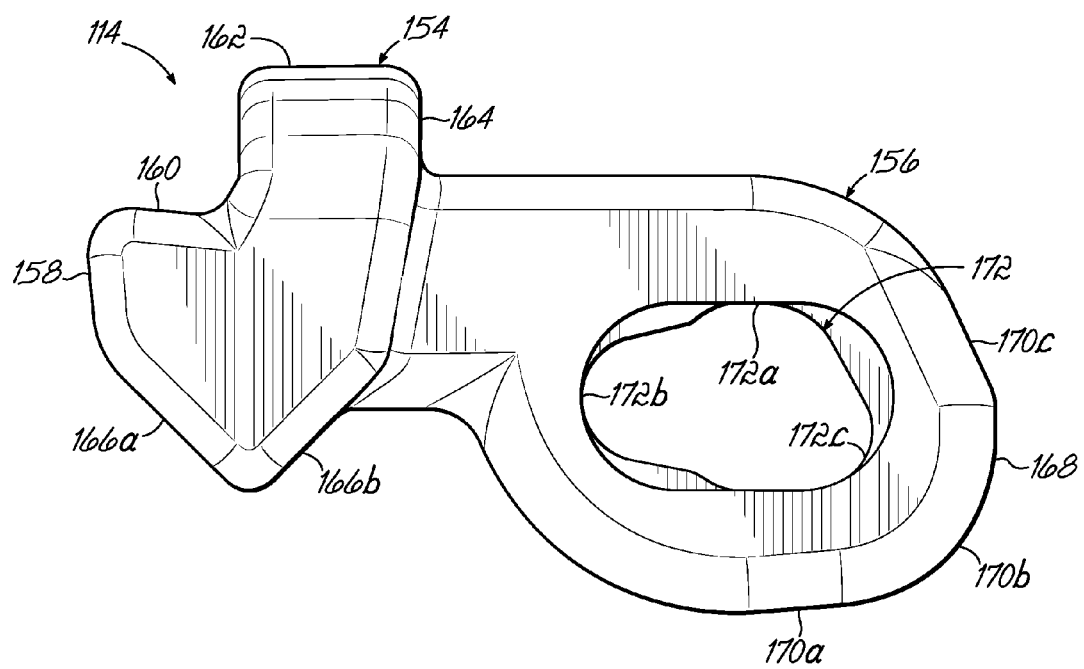
FIG. 3A is a side elevation view of the ligating latch shown in FIG. 3

Referring now to the drawings and to FIGS. 1 and 2 in particular, one embodiment of a self-ligating orthodontic bracket 110 includes a bracket body 112 and a movable ligating latch 114 operably coupled to the bracket body 112 by a resilient hinge pin 116 (shown in FIG. 2). The orthodontic bracket 110 is configured for use in corrective orthodontic treatments. To that end, the bracket body 112 includes an archwire slot 118 formed therein that is adapted to receive an archwire (not shown) for applying corrective forces to the teeth. The ligating latch 114 is movable between a closed position (FIG. 1) in which the ligating latch 114 retains the archwire within the archwire slot 118 and an open position (FIG. 2) in which the archwire is insertable into the archwire slot 118. The movement of the latch 114 from the closed position to the opened position may require a combination of rotational motion around an axis of rotation 117 determined by the hinge pin 116 and relative translational motion between the latch 114 and the bracket body 112. By way of example, translational motion may include non-collinear movement relative to the axis of rotation. By way of further example, non-collinear movement may include one or more directions that are substantially perpendicular to the axis of rotation 117. As is set forth in detail below, the ligating latch 114 may be securely held in the open and the closed positions by interaction with the resilient hinge pin 116. Such interaction may include deformation of the cross-sectional profile of the hinge pin 116. This operation improves upon conventional self-ligating brackets such as the bracket disclosed in U.S. Pat. No. 7,674,110 to Oda, the disclosure of which is hereby incorporated by reference in its entirety.

The orthodontic bracket 110 of this embodiment and the orthodontic brackets of other embodiments, unless otherwise indicated, are described herein using a reference frame attached to a lingual surface of a tooth on the upper or lower jaw. Consequently, terms such as labial, lingual, mesial, distal, occlusal, and gingival used to describe the orthodontic bracket 110 are relative to the chosen reference frame. The embodiments of the invention, however, are not limited to the chosen reference frame and descriptive terms, as the orthodontic bracket 110 may be used on other teeth and in other orientations within the oral cavity. For example, the orthodontic bracket 110 may also be coupled to the labial surface of the tooth and be within the scope of the invention. Those of ordinary skill in the art will recognize that the descriptive terms used herein may not directly apply when there is a change in reference frame. Nevertheless, the embodiments of the invention are intended to be independent of location and orientation within the oral cavity and the relative terms used to describe embodiments of the orthodontic bracket are to merely provide a clear description of the embodiments in the drawings. As such, the relative terms labial, lingual, mesial, distal, occlusal, and gingival are in no way limiting embodiments of the invention to a particular location or orientation.

One embodiment of the orthodontic bracket 110 is particularly configured for use on the lingual surface of an anterior tooth on the upper jaw. In this regard, the overall shape and profile of the orthodontic bracket 110 may generally correspond to the shape of anterior teeth on the upper jaw. When mounted to the lingual surface of an anterior tooth carried on the patient's upper jaw, the bracket body 112 has a lingual side 120, an occlusal side 122, a gingival side 124, a mesial side 126, a distal side 128, and a labial side 130. The labial side 130 of the bracket body 112 is configured to be secured to the tooth in any conventional manner, such as, by an appropriate orthodontic cement or adhesive or by a band around an adjacent tooth. In the illustrated arrangement, the labial side 130 may include a shaped projection 132 (shown in phantom line in FIG. 2) configured for insertion and coupling with a corresponding receptacle formed on a pad (not shown) defining a bonding base that is secured to the surface of the tooth. The pad may be coupled to the bracket body 112 as a separate piece or element (e.g., by laser or other conventional welding processes), and may be specially formed for a particular patient. For example, the pad may be customized to fit the surface of a particular patient's tooth while positioning the archwire slot relative to the tooth surface. In this regard, impressions of the patient's tooth are obtained and are then scanned or digitized for manipulation with a computer. With computer manipulated data of the patient's tooth, a pad is manufactured such that the surface thereof mates with that tooth. The pad may be manufactured via direct metal manufacturing or other similar method where metal powder is sintered or bonded together with a laser. The laser and/or powder are directed by the computer manipulated data of the patient's tooth surface to prepare the surface and thickness of the pad for that patient. It will be appreciated that the shaped projection 132 may define a generally trapezoidal shape to fit within a similarly shaped recess in the custom manufactured pad.

The bracket body 112 may include a gingival tie wing 134 extending in a gingival direction at the lingual side 120. The bracket body 112 may also include a pair of occlusal tie wings (not shown) extending in an occlusal direction at the lingual side 120. In the exemplary embodiment, the bracket 110 may be configured to be narrower in width towards the gingival side 124, to thereby correlate to the shape of anterior teeth on the upper jaw. To this end, the bracket body 112 may taper slightly to become narrower in the mesial-distal direction toward the gingival side 124. In this regard, one of ordinary skill in the art will appreciate that embodiments of the present invention are not limited to a particular overall configuration or profile of the bracket body as the shape or general profile of the bracket 110 may take many forms and may be configured to fit onto a particular tooth surface.

The bracket body 112 defines a central space 138 therein that is configured to receive the ligating latch 114. For example, the central space 138 may be bounded on mesial and distal sides by generally parallel mesial and distal internal surfaces 139a, 139b formed in the bracket body 112. The central space 138 is bounded on a labial side by a first cam surface 140 (shown best in FIGS. 4A-5B and described in more detail below) formed on the lingual side 120 of the bracket body 112. The central space 138 may communicate with the archwire slot 118. The archwire slot 118 extends from the mesial side 126 to the distal side 128 of the bracket body 112 and is generally angled so as to be gingivally biased. The archwire slot 118 may be bowed or arched so as to form a generally concave surface that may conform generally to the archwire curvature when it is installed therein. The gingival bias of the archwire slot 118 facilitates straight wire mechanics during lingual treatment of teeth. Straight wire mechanics in such an application are further explained by U.S. Pat. No. 6,264,468 to Takemoto, the disclosure of which is hereby incorporated by reference in its entirety. The archwire slot 118 is defined by three generally perpendicular sides referred to herein as the gingival slot side 142a, the labial slot side 142b, and the occlusal slot side 142c. However, it will be understood that the archwire slot 118 opens in a generally occlusal-lingual direction because of the gingival bias.

With reference to FIG. 2, the gingival slot side 142a includes a lingual edge 144. The lingual edge 144 defines one side of a generally triangular-shaped recess 146 formed in the bracket body 112 adjacent to and in a lingual direction from the archwire slot 118. The triangular-shaped recess 146 is formed between the lingual edge 144 of the gingival slot side 142a and an overhanging lip 148 at the lingual side 120 of the bracket body 112. The triangular-shaped recess 146 and overhanging lip 148 are configured to engage with the ligating latch 114 in the closed position, as explained in further detail below.

As shown in FIG. 1, the lingual side 120 of the bracket body 112 may further include a tool slot 150 formed between the mesial side 126 and the distal side 128 at the overhanging lip 148. The tool slot 150 provides ready access for an opening tool to engage the top of the ligating latch 114 in the closed position. The tool slot 150 also divides the overhanging lip 148 into a mesial lip portion 148a and a distal lip portion 148b.

With reference to FIG. 2, the occlusal slot side 142c of the exemplary embodiment shown does not continuously extend to the lingual side 120 of the bracket body 112. Instead, the occlusal slot side 142c terminates at a lingual edge 178 corresponding to the lingual edge 144 of the gingival slot side 142a. The bracket body 112 further includes an angled lingual surface 180 extending from the lingual side 120 of the bracket body 112 to a shoulder 182 formed proximate to the lingual edge 178 of the occlusal slot side 142c. It will be appreciated that embodiments of the invention are not so limited as the occlusal slot side 142c may extend continuously beyond the archwire slot 118 to the lingual side 120 of the bracket body 112.

The bracket body 112 further includes a generally circular cross-section mesial-distal through-bore 152 located in an occlusal direction from the archwire slot 118 and the triangular-shaped recess 146 and in a gingival direction from the occlusal side 122 of the bracket body 112. The through-bore 152 intersects and is divided by the central space 138. The resilient hinge pin 116 is placed into the through-bore 152 in the bracket body 112 to thereby define a pivot point or hinge for the ligating latch 114. In this regard, a portion of the hinge pin 116 extends across the central space 138 between the mesial and distal internal surfaces 139a, 139b of the bracket body 112. A portion of the hinge pin 116 may be slidably engaged in the through-bore 152 such that the hinge pin 116 may slide or rotate with respect to the bracket body 112. In some embodiments, the bracket body 112 may be slightly deformed in the area of the through-bore 152 after the hinge pin 116 is positioned in the through-bore 152, thereby slightly deforming the circular cross-section of the through-bore 152. This slightly deformed cross-section of the through-bore 152 would tend to prevent sliding movement in the mesial-distal direction of the hinge pin 116 with respect to the bracket body 112 to prevent the pin 116 from inadvertently working its way out of the bracket body 112. However, this slight deformation is not illustrated in the embodiment of FIGS. 1-2.

The hinge pin 116 is generally a hollow cylindrical member composed of a resilient or superelastic material. In an exemplary embodiment, the hinge pin 116 is composed of Nickel Titanium (NiTi) superelastic material. By way of example, one NiTi composition includes about 55 wt. % nickel (Ni), and about 45 wt. % titanium (Ti) with minor amounts of impurities and which is available from NDC of Fremont, Calif. The mechanical properties of the NiTi alloy may include an ultimate tensile strength of greater than about 155 ksi, an upper plateau of greater than about 55 ksi, and a lower plateau of greater than about 25 ksi. The dimensions of the hinge pin 116 may vary depending on the size of the bracket itself. By way of example, a diameter of a circular cylindrical hinge pin may vary from about 0.0145 inch to about 0.0175 inch, and by way of further example, from about 0.0155 inch to about 0.0165 inch. The thickness of the side wall of a circular cylindrical hinge pin may vary from about 0.001 inch to about 0.003 inch, and by way of additional example, from about 0.001 inch to about 0.0025 inch. Once assembled in a bracket, the latch may be opened and closed a few times (e.g., three times) before the force to open and close the latch approaches that desired for clinical use.

The bracket body 112 and the ligating latch are generally composed of a relatively non-resilient structural material such as 17-4 stainless steel. Alternative materials may be used for the bracket body 112, the ligating latch 114, and the hinge pin 116 in other embodiments within the scope of this invention. Consequently, the hinge pin 116 is held in the bracket body 112 at the through-bore 152, but is configured to elastically deform in the central space 138 in the advantageous operation of the ligating latch 114 described below.

As shown in FIGS. 2, 3, 3A, and 4A, the ligating latch 114 includes a tip portion 154 and a pivot portion 156. The tip portion 154 extends mesially-distally across substantially the entire width of the bracket body 112. As is shown best in FIGS. 2 and 4A, the tip portion 154 includes a gingival side 158, a lingual side 160 including an outwardly-extending projection 162, an occlusal side 164, and first and second labial sides 166a, 166b extending respectively from the gingival side 158 and the occlusal side 164. In the closed position, shown in FIG. 4A, the gingival side 158 of the tip portion 154 is configured to seat generally within the triangular-shaped recess 146 in the bracket body 112 such that the lingual side 160 of the tip portion 154 is located underneath the overhanging lip 148. The outwardly-extending projection 162 is configured to be adjacent to the overhanging lip 148 in the closed position, while the occlusal side 164 faces toward the hinge pin 116 and the central space 138. The first labial side 166a of the tip portion 154 extends generally parallel to the labial slot side 142b of the archwire slot 118 and is configured to close the opening of the archwire slot 118. The second labial side 166b of the tip portion 154 extends generally parallel to the occlusal slot side 142c of the archwire slot 118 but remains spaced from the occlusal slot side 142c in the closed position. In embodiments in which the occlusal slot side 142c does not extend to the lingual side 120, the tip portion 154 of the ligating latch 114 may be formed with a first labial side 166a sized to adjust a gap between the second labial side 166b and the occlusal slot side 142c of the archwire slot 118. It will be appreciated that the gap size may be dimensioned to discourage an archwire from moving out of the archwire slot 118 into the gap during orthodontic treatment.

With continued reference to FIGS. 1, 3, 3A, and 4A, the pivot portion 156 of the ligating latch 114 extends in an occlusal direction from the occlusal side 164 of the tip portion 154. The pivot portion 156 is defined by a generally oblong cross-section that extends in a mesial-distal direction between the mesial and distal internal surfaces 139a, 139b of the bracket body 112 so as to fit within the central space 138, as shown best in FIG. 1. The pivot portion 156 includes a rounded outer periphery 168 defining a second cam surface 170 with a first portion 170a, a transition portion 170b, and a second portion 170c. The pivot portion 156 also includes a mesial-distal oblong pin aperture 172. Generally, the aperture 172 differs in shape from the cross-sectional profile of the hinge pin 116. In other words, the cross-sectional profiles of each may be substantially non-congruent. By contrast, the bore 152 may be substantially congruent with the cross-sectional profile of the pin 116. The oblong pin aperture 172 includes a central portion 172a, a first narrowed end 172b extending toward the tip portion 154 of the ligating latch 114, and a second narrowed end 172c extending in an opposite direction generally toward the transition portion 170b of the second cam surface 170. The oblong pin aperture 172 is configured to receive the hinge pin 116 and interact with, so as to elastically deform, the hinge pin 116 as the ligating latch 114 moves between the open and closed positions. To this end, and by way of example, the overall configuration of the aperture 172 may include a non-symmetric cross-sectional profile, for instance, an egg-shaped type cross-sectional profile encompassing the central portion 172a and the first narrowed end 172b or a double egg-shaped type cross-sectional profile when all of the portions 172a, 172b, and 172c are collectively encompassed. It will be appreciated that while the aperture 172 is described as having a particular cross-sectional profile that differs from the corresponding portion of the pin 116, and the bore 152 is described substantially matching the size of the pin 116, the shapes of the pin aperture 172 and the bore 152 may be reversed. That is, the bore 152 may be oblong shaped with the pin aperture 172 sized to match the outside diameter of the pin 116 without departing from the scope of the embodiments disclosed herein.

Figure 4A:
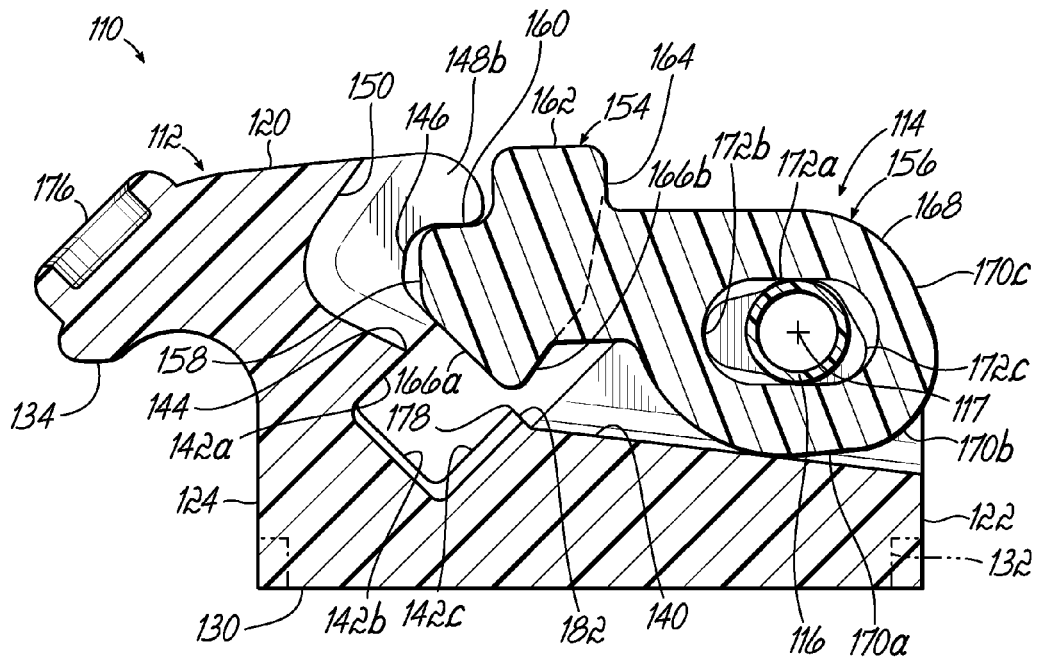
FIG. 4A is a cross-sectional side view of the self-ligating orthodontic bracket shown in FIG. 1, with the ligating latch in the closed position.
Figure 5A:
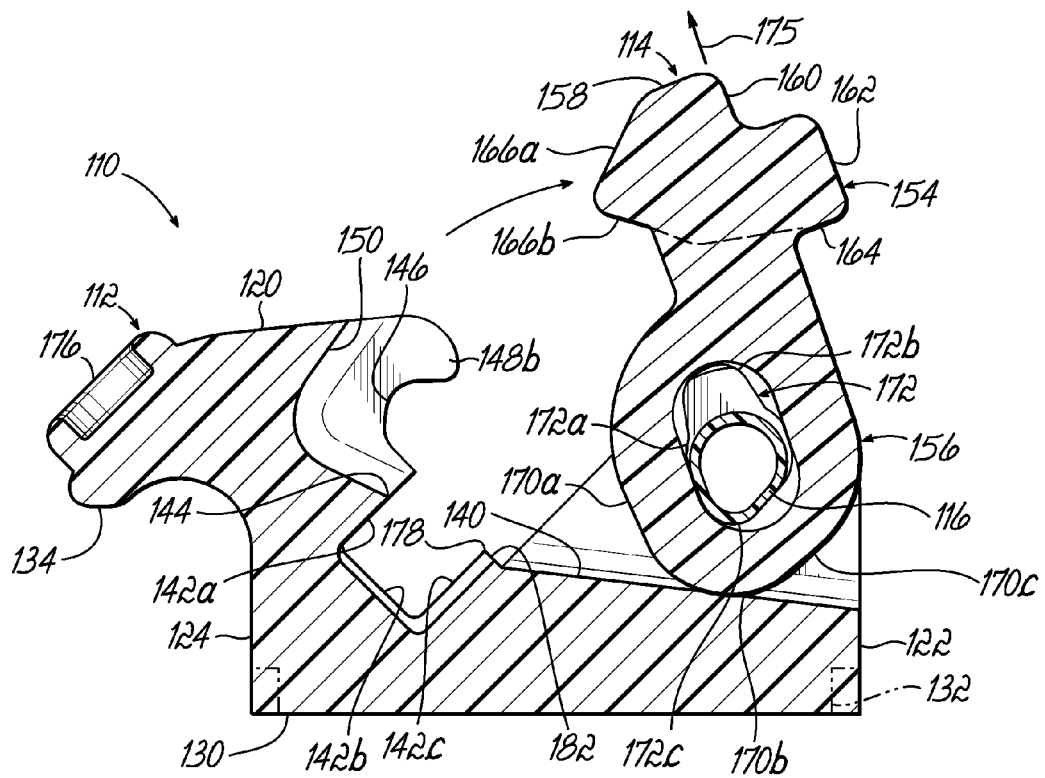
FIG. 5A is a cross-sectional side view of the self-ligating orthodontic bracket shown in FIG. 1, with the ligating latch rotated from the position shown in FIG. 4B.
Figure 5B:
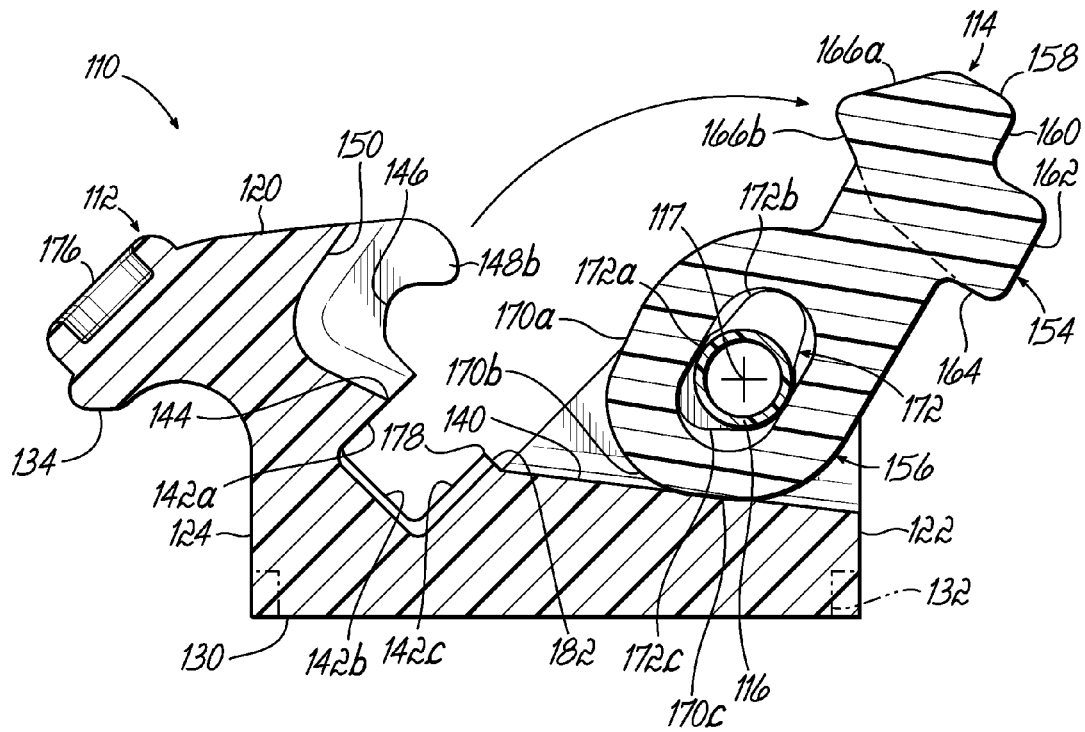
FIG. 5B is a cross-sectional side view of the self-ligating orthodontic bracket shown in FIG. 1, with the ligating latch rotated from the position shown in FIG. 5A.

To this end, in one embodiment, the ligating latch 114 and bracket body 112 engage in a unique cam relationship such that the hinge pin 116 effectively holds the ligating latch 114 in the closed position (FIG. 4A) or the opened position (FIG. 5B). As shown in FIG. 4A, the hinge pin 116 is located in the central portion 172a of the pin aperture 172 in the closed position. The central portion 172a may be designed to be slightly narrower than the unbiased or relaxed-state diameter of the hinge pin 116 such that the hinge pin 116 is slightly compressed in the closed position. The first portion 170a of the second cam surface 170 on the ligating latch 114 may be engaged with the first cam surface 140 on the bracket body 112 in this position, and the gingival side 158 of the tip portion 154 of the ligating latch 114 is disposed underneath the overhanging lip 148 as previously described.

Figure 4B:
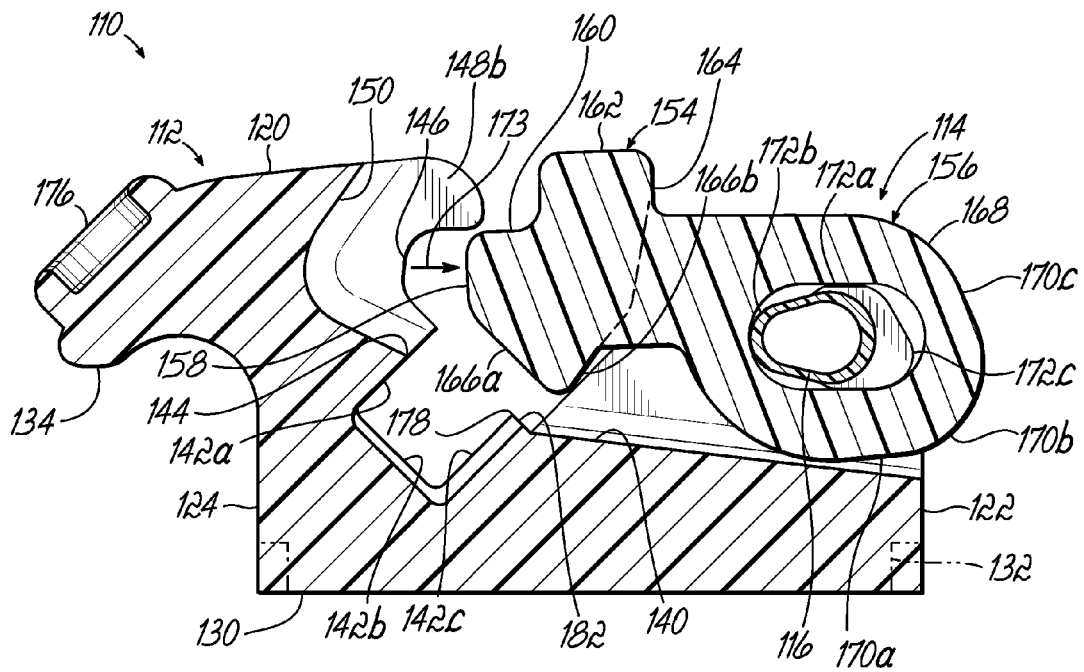
FIG. 4B is a cross-sectional side view of the self-ligating orthodontic bracket shown in FIG. 1, with the ligating latch translated in one direction relative to that shown in FIG. 4A.

With reference to FIG. 4B, to move the ligating latch 114 from the closed position, a tool (not shown) such as a scaler-type tool or a rotational tool with a flat head (i.e., screwdriver) may be inserted into the tool slot 150 of the bracket body 112 so as to force the ligating latch in an occlusal direction or toward the occlusal side 122. The latch 114 may therefore be displaced from the closed position along a direction (indicated by arrow 173) relative to the bracket body 112. The hinge pin 116 may be elastically deformed along its cross-sectional profile as the pin 116 is forced into the first narrowed end 172b of the pin aperture 172 as the ligating latch 114 is moved in the occlusal direction. This deformation may include elastically deforming a generally circular cross-sectional profile of a portion of the hinge pin 116 in the central portion 172a into an oblong cross-sectional profile when in the first narrowed end 172b. In one embodiment, the profile of the first narrowed end 172b may be imposed on a corresponding portion of the hinge pin 116 such that the cross-sectional profiles may conform to one another. It will be appreciated that other configurations of the first narrowed end 172b may be utilized to elastically deform the hinge pin 116.

Once the gingival side 158 of the tip portion 154 is translated beyond the overhanging lip 148 on the bracket body 112, the tool may begin to rotate the ligating latch 114 with respect to the hinge pin 116 to move or rotate the tip portion 154 away from the archwire slot 118. As will be readily understood, the hinge pin 116 immediately expands back into the central portion 172a of the pin aperture 172 after the rotating tip portion 154 clears the overhanging lip 148. That is, the portion of the hinge pin 116 that was in the first narrowed end 172b may elastically recover the cross-sectional profile it had while the latch 114 was in the closed position. The second labial side 166b of the tip portion 154 may not come into contact with the occlusal slot side 142c at any point during this movement from the closed position. Consequently, the elastic deformation of the resilient hinge pin 116 within the pin aperture 172 holds the ligating latch 114 in the closed position until a tool forces the hinge pin 116 to deform in the pin aperture 172 as described above, although the engagement of the lingual side 160 of the tip portion 154 and the overhanging lip 148 on the bracket body 112 may also help hold the ligating latch 114 in the closed position.

With reference now to FIG. 5A, as the ligating latch 114 continues to be rotated about an axis of rotation determined by the hinge pin 116, the transition portion 170b of the second cam surface 170 on the ligating latch 114 begins to slide against the first cam surface 140 in the bracket body 112. The transition portion 170b of the second cam surface 170 projects outwardly compared to the first and second portions 170a, 170c of the second cam surface 170. Therefore, as the transition portion 170b rotates against the first cam surface 140, the ligating latch 114 is forced in direction that translates the latch 114 relative to the bracket body 112. This may be in a direction that is non-collinear with the axis of rotation 117. For example, the latch 114 may be forced in a lingual direction (as depicted by the arrow 175) such that the hinge pin 116 compresses or elastically deforms into the second narrowed end 172c of the pin aperture 172. As described above, elastic deformation may include elastic deformation of the cross-sectional profile of the hinge pin 116 as it is forced into the second narrowed end 172c.

With reference to FIG. 5B, as the ligating latch 114 then rotates further so that the second portion 170c of the second cam surface 170 comes into engagement with the first cam surface 140, the hinge pin 116 expands or elastically recovers back into the central portion 172a of the pin aperture 172 in the opened position of FIGS. 2 and 5B. Consequently, the deformation of the resilient hinge pin 116 within the pin aperture 172 holds the ligating latch 114 in the opened position until a clinician rotates the ligating latch 114 with enough force to deform the hinge pin 116 into the second narrowed end 172c of the pin aperture 172. This operation is advantageous because gravity may tend to automatically close the ligating latch 114 in the brackets 110 affixed to the lower jaw without the hinge pin 116 holding the ligating latch 114 in the open position.

To summarize the operation, the resilient hinge pin 116 is compressed or elastically deformed by the pin aperture 172 in the ligating latch 114 such that the ligating latch 114 is advantageously held in either the closed position of FIG. 4A or the opened position of FIG. 5B. To move the ligating latch 114 from the closed position to the open position, a tool inserted into the tool slot 150 must force the ligating latch 114 past and around the overhanging lip 148 on the bracket body 112 by deforming the hinge pin 116 into the first narrowed end 172b of the pin aperture. Then, the tool or a finger may be used to force the latch 114 in a rotational direction to deform the hinge pin 116 into the second narrowed end 172c of the pin aperture 172 as the transition portion 170b of the second cam surface 170 on the ligating latch 114 engages the first cam surface 140. To move the ligating latch 114 from the opened position to the closed position, a clinician may push on the outwardly-extending projection 162 of the tip portion 154 of the ligating latch 114 to rotate the ligating latch 114 about the hinge pin 116 in the opposite direction. The first labial side 166a will abut the overhanging lip 148 on the bracket body 112 as the ligating latch 114 approaches the closed position, but the smooth angled contour of the first labial side 166a is configured to cam the ligating latch 114 in an occlusal direction as the clinician applies force on the outwardly-extending projection 162, thereby permitting the ligating latch 114 to return to the closed position without the use of a specialized tool. In this regard, the outwardly-extending projection 162 provides a particular tactile feel for the clinician to find the ligating latch 114 easily and move the ligating latch 114 toward the closed position, even with the reduced visibility of the bracket 110 in a lingual application.

When the ligating latch 114 is in the opened position, the generally occlusal opening direction of the archwire slot 118 permits a clinician to "drop-in" the archwire easily into the archwire slot 118. The archwire is also easy to remove from the bracket 110 when replacement or adjustment of an archwire is necessary.

In one embodiment, shown in FIG. 2, an optional ball-shaped member 174 (shown in phantom line) is engaged with the bracket body 112 at the mesial side 126 to close off the bore 152. Although not shown, another ball-shaped member may be similarly placed on the distal side 128 of the bracket body 112. The ball-shaped members 174 may be slightly deformed such that the ball-shaped members 174 are held by a friction fit in the bracket body 112. The optional ball-shaped members close off the open passage through a hollow hinge pin and generally prevent food or other substances from becoming lodged in the hinge pin 116, which could affect the performance of the bracket 110.

The advantageous hinging mechanism provided in the central space 138 between the mesial and distal internal surfaces 139a, 139b of the bracket body 112 permits the bracket 110 to be formed with an overall reduced mesial-distal width compared to conventional self-ligating brackets. To this end, the reduced overall width of the bracket 110 is ideally configured for use on the lingual surfaces of anterior teeth, which have a much smaller bonding area than corresponding buccal or labial surfaces of anterior teeth. However, as noted above, the bracket 110 may be applied to any number of teeth on the upper or lower jaw as well as on the labial side of a tooth without departing from the scope of the invention described herein.

In one embodiment, as shown in FIG. 1, the gingival tie wing 134 of the bracket 110 includes a mounting depression 176 having a generally standardized circular cross-section. The mounting depression 176 is configured to receive an auxiliary member such as a hook (not shown) when the orthodontic treatment requires an auxiliary member. The auxiliary member is not typically engaged with the mounting depression 176 prior to use because the available space in the mouth around the gingival side 124 of the bracket 110 is limited. The connection of an auxiliary member with the standardized mounting depression 176 is well-understood in the art and not further described here.

Also illustrated in FIG. 1, in one embodiment a pair of occlusal tie wings 136 extend in respective mesial and distal directions from the lingual side 120 of the bracket body 112 at the occlusal side 122, rather than extending in an occlusal direction as described above. In order to ensure an adequate amount of space is provided under the occlusal tie wings 136 for tying a ligature or other member to the bracket 110, the width of the bracket body 112 steps slightly inwardly at external shoulders 184 formed on the mesial side 126 and the distal side 128 of the bracket body 112. The narrowing of the bracket body 112 is most clearly shown in FIG. 1. However, the overall mesial-distal width of the bracket 110 is advantageously configured and shaped for application to the lingual side of an anterior tooth on the upper jaw.

Figure 6:
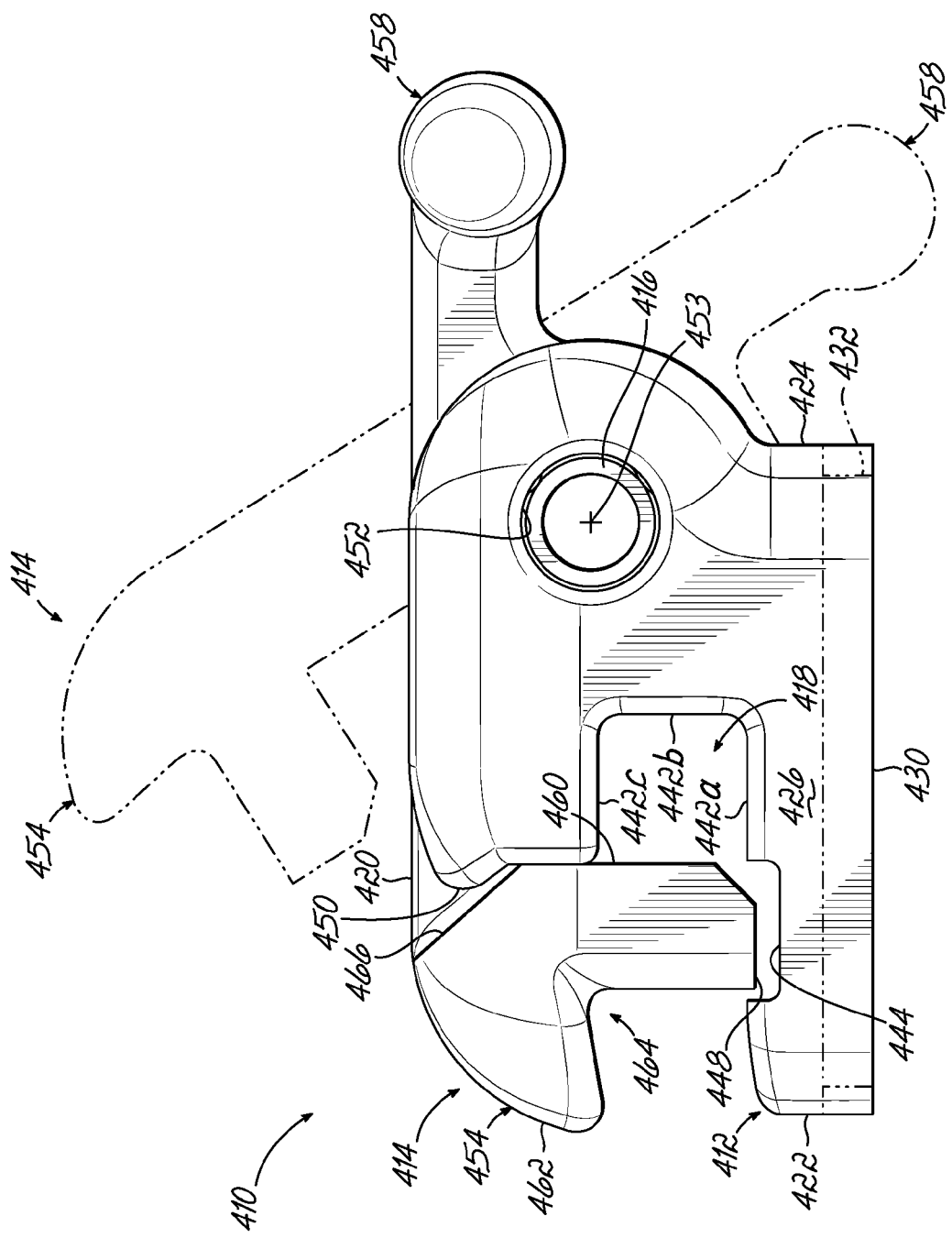
FIG. 6 is a side elevation view of a self-ligating orthodontic bracket in accordance with one embodiment of the invention, with a ligating latch shown in a closed position.
Figure 7:
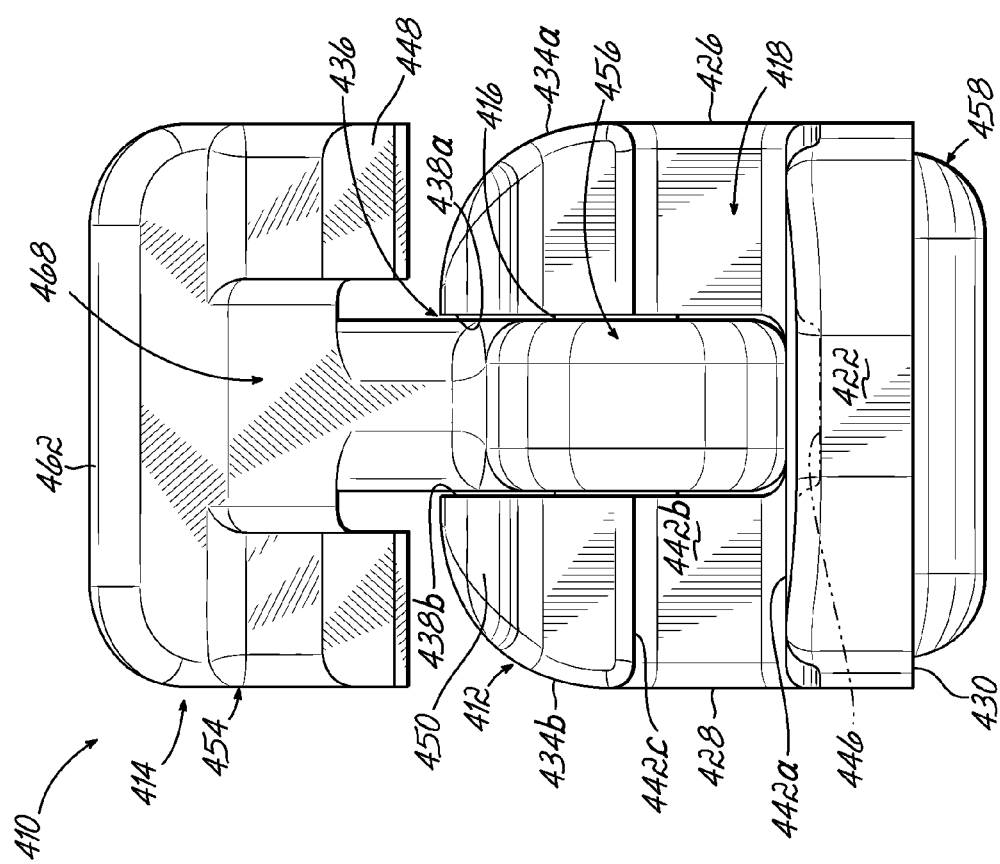
FIG. 7 is a front elevation view of the self-ligating orthodontic bracket shown in FIG. 6, with the ligating latch in the opened position.
Figure 8:
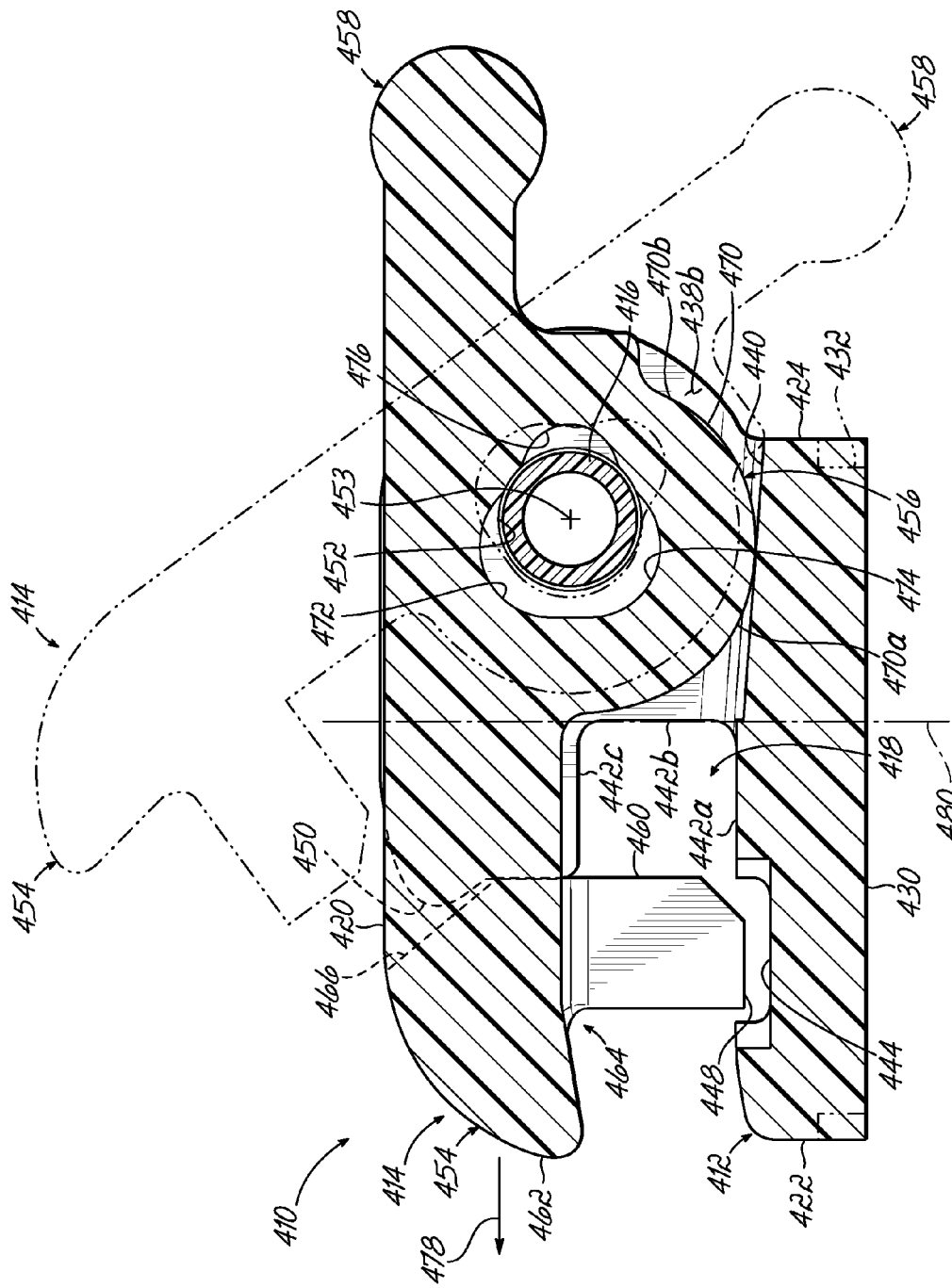
FIG. 8 is a cross-sectional side view of the self-ligating orthodontic bracket shown in FIG. 6, with the ligating latch in the closed position.

Another embodiment of a self-ligating orthodontic bracket 410 of this invention is illustrated in FIGS. 6-8. This embodiment of the orthodontic bracket 410 is configured for use on the lingual side of bicuspid teeth in the upper or lower jaw. Similar to the previous embodiments, the bracket 410 includes a bracket body 412 and a ligating latch 414 coupled to the bracket body 412 by a hinge pin 416. The ligating latch 414 is configured to move between a closed position and an opened position (shown in phantom line). In the closed position, the ligating latch 414 closes an archwire slot 418 formed in a mesial-distal direction through the bracket body 412. In the opened position, the ligating latch 414 moves away from the archwire slot 418 so that an archwire may be positioned within the archwire slot 418 or removed from the archwire slot 418. As set forth in further detail below, the ligating latch 414 is held in the closed position or the opened position by interaction with the resilient hinge pin 416. Similar to the previous embodiments, the hinge pin 416 may be composed of a superelastic NiTi material and the bracket body 412 and the ligating latch 414 may be composed of 17-4 stainless steel.

Generally speaking, bicuspid teeth do not provide strict size limitations on the orthodontic bracket 410, so the bracket body 412 has the general shape of a rectangle. The shape of the bracket body 412 may be modified without departing from the scope of this invention. Regardless of whether the bracket 410 is mounted on a tooth in the upper jaw or the lower jaw, the bracket body 412 includes a lingual side 420, an occlusal side 422, a gingival side 424, a mesial side 426, a distal side 428, and a labial side 430. The labial side 430 is again configured to be coupled with a lingual surface of a tooth, and may include a shaped projection 432 for insertion into a corresponding receptacle formed on a pad (not shown) secured to the tooth. The shaped projection 432 is shown in phantom line in FIGS. 6 and 8 and may be coupled to the pad by any known coupling method, including lasering and welding.

In the exemplary embodiment shown, the orthodontic bracket 410 does not include any tie wings. Instead, the bracket body 412 includes a pair of outwardly-projecting body portions 434a, 434b partially defining the archwire slot 418 and extending in an occlusal-gingival direction from the archwire slot 418 to the gingival side 424 of the bracket body 412. The pair of body portions 434a, 434b is spaced from each other so as to define a central space 436 extending in an occlusal-gingival direction across the lingual side 420 of the bracket body 412. The pair of body portions 434a, 434b includes generally parallel inwardly-facing surfaces 438a, 438b which define the mesial-distal width of the central space 436. The central space 436 is also bounded by a first cam surface 440 (FIG. 8) formed in the bracket body 412 between the inwardly-facing surfaces 438a, 438b.

The archwire slot 418 is defined by a labial slot side 442a, a gingival slot side 442b, and a lingual slot side 442c. As most clearly shown in FIGS. 7 and 8, the gingival slot side 442b and the lingual slot side 442c are defined by the pair of body portions 434a, 434b. Consequently, the archwire slot 418 opens in a generally occlusal direction. An archwire may again be "dropped-in" or easily positioned in the archwire slot 418 when the ligating latch 414 is in the open position, as previously described with respect to other embodiments. The bracket body 412 includes a latch slot 444 and may include and a tool slot 446 (shown in phantom line in FIG. 7) machined into the lingual side 420 proximal to the occlusal side 422 of the bracket body 412. The latch slot 444 extends in a mesial-distal direction across the width of the bracket body 412 and is configured to receive a leading edge 448 of the ligating latch 414 as described in further detail below. The latch slot 444 is directly adjacent to and occlusal from the labial slot side 442a. When present, the tool slot 446 may extend in an occlusal-gingival direction and extend from the occlusal side 422 of the bracket body 412 to at least the latch slot 444. The tool slot 446 is configured to receive a portion of a tool used to pry the ligating latch 414 away from the closed position.

The body portions 434a, 434b further define an occlusally-extending shoulder 450 projecting above the archwire slot 418 at the lingual side 420. The shoulder 450 and the hinge pin 416 are configured to cooperate with the ligating latch 414 to hold the ligating latch 414 in the opened position or the closed position. The body portions 434a, 434b also include a generally circular cross-section mesial-distal through-bore 452 located in a lingual direction from the first cam surface 440 and in a labial direction from the lingual side 420 of the bracket body 412. Similar to other embodiments, the through-bore 452 is configured to receive the resilient hinge pin 416 such that the hinge pin 416 extends across the central space 436 as a pivot point for the ligating latch 414 and generally defines an axis of rotation 453. The hinge pin 416 is held in the through-bore 452 by a frictional fit or an interference fit caused by slight deformation (not shown in the illustrated embodiment) of the bracket body 412 applied after the hinge pin 416 is inserted into the through-bore 452.

The ligating latch 414 includes a closure portion 454, a pivot portion 456, and an auxiliary portion 458 disposed on the opposite side of the pivot portion 456 from the closure portion 454. The closure portion 454 extends in a mesial-distal direction across the width of the bracket body 412 and defines a generally L-shaped cross-section. With respect to the closed position shown in FIGS. 6 and 8, the closure portion 454 includes a gingival side 460, an occlusal side 462, and the leading edge 448. A portion of the occlusal side 462 of the closure portion 454 may be machined off to define an optional tie wing-like cavity 464 in the closure portion 454. In this regard, the cavity 464 may receive a ligature or another device typically coupled to a tie wing. The leading edge 448 is configured to be disposed in the latch slot 444 of the bracket body 412 in the closed position, as shown. The gingival side 460 of the closure portion 454 is configured to close off the occlusal side of the archwire slot 418 in the closed position. The gingival side 460 further includes a pair of angled relief portions 466 in a near-abutting or abutting relation with the angled contour of the shoulder 450 on the bracket body 412 in the closed position. The closure portion 454 also includes a tool slot 468 adjacent to the cavity 464 and in communication with the tool slot 446 in the bracket body 412.

With reference to the embodiment shown in FIG. 8, the pivot portion 456 includes a second cam surface 470 formed along the outer periphery, and further includes a pin aperture 472 configured to receive the hinge pin 416. The second cam surface 470 includes a rounded portion 470a and a flattened portion 470b each configured to slide against or engage with the first cam surface 440 on the bracket body 412 during movement of the ligating latch 414. The auxiliary portion 458 is formed as a capsule-shaped mesial-distal extending member configured to receive ligatures or other auxiliary attachment devices. As such, the cavity 464 in the closure portion 454 and the auxiliary portion 458 effectively replace the tie wings of the previous embodiments. It will be appreciated, however, that the tie wing-like cavity 464 in combination with the auxiliary portion 458 may be utilized to prevent inadvertent opening of the latch 414 when power chains and the like are attached to the bracket 410. In this regard, the loads from a power chain may be more equally distributed on the latch 414. Specifically, loads may be distributed on both sides of the pin 416 and may keep the net torque about the pin 416 to a minimum. Thus, the latch 414 is less likely to open under these circumstances.

In one embodiment, the pin aperture 472 includes a relatively oblong central portion 474, the longitudinal axis of which may be oriented in the labial-lingual direction and may include a lobe-shaped portion 476 that is contiguous with the oblong central portion 474. The oblong central portion 474 may ease assembly of the pin 416 in the bracket body 412. Generally, the cross-sectional profile of the pin aperture 472 may be substantially non-congruent with the corresponding cross-sectional profile of the hinge pin 416 and may be non-symmetric relative to the bore 452, similar to that set out above. In this regard, the outer periphery of the hinge pin 416 may not contact the pin aperture 472 at all locations there along. In one embodiment, at least the thickness of the pin 416 is greater than the pin 116 set out above. The increased thickness may increase the resistance of the latch 414 to inadvertently opening under load of an archwire in the archwire slot. It will be appreciated that the latch 414 may experience relatively greater loads as compared to the latch 114 because of the relative orientation of the archwire slots 118, 418. The archwire slot 118 is oriented generally in an occlusal-lingual direction whereas the archwire slot 418 is oriented more in an occlusal-gingival direction and thus greater loads may be experienced by the latch 414. In one embodiment, the pin aperture 472 is slightly narrower in one direction than the relaxed-state diameter of the hinge pin 416 such that the hinge pin 416 is continuously compressed or elastically deformed in the central space 436. Similarly, in one embodiment, the pin 416 contacts a gingival portion of the aperture 472 when the latch 414 is in the closed position and may be under load while in this position. This loaded or non-relaxed state of the pin 416 in this position may be advantageous. In this regard, the pin 416, when under a preload, may keep the latch 414 in the closed position at greater loads than are likely to be experienced by the latch 414 in this location. Furthermore, loading the pin 416 may keep the latch 414 in a direct abutting relationship with the bracket body 412 near the shoulder 450, as shown, and thus may bias the latch 414 in a direction that intersects a plane 480 that includes the gingival slot side 442. This may reduce the variation in tolerances observed in the archwire slot 418 and produce a more consistent occlusal-gingival dimension of the archwire slot 418.

Referring to FIG. 8, the ligating latch 414 cooperates with the bracket body 412 in a unique cam relationship such that the ligating latch 414 may be held in the closed position or the opened position. In the closed position, the angled relief portions 466 of the gingival side 460 of the closure portion 454 may abut or be in abutting relationship with the shoulder 450 on the bracket body 412 to resist inadvertent opening of the latch 414. Furthermore, the rounded portion 470a of the second cam surface 470 may be engaged with the first cam surface 440 on the bracket body 412.

To move the ligating latch 414 from the closed position to the opened position, a tool such as a flat-head screwdriver is inserted into the tool slot 468, and optional tool slot 446, and translated in a direction (shown by arrow 478) that translates the latch 414 relative to the bracket body 412. For example, relative translation movement may include movement in an occlusal direction relative to the axis of rotation 453. By such movement, the pin 416 elastically deforms into the lobe-shaped portion 476 and the relief portions 466 clear the shoulder 450 in the occlusal direction. The latch 414 may then be rotated or moved about the axis of rotation 453. In one embodiment, the latch 414 may be moved from the closed position by engaging the tool in the slot 468 so as to force the closure portion 454 toward the shoulder 450. The angled relief portions 466 may be forced to slide up the shoulder 450, which translates the ligating latch 414 in an occlusal direction and forces the hinge pin 416 to further compress or deform within the pin aperture 472.

With continued reference to FIG. 8, directly after the angled relief portions 466 clear the shoulder 450, the rotation of the pivot portion 456 of the ligating latch 414 will cause the flattened portion 470b of the second cam surface 470 to engage the first cam surface 440 to thereby block further rotation of the ligating latch 414 in the gingival direction. The hinge pin 416 may elastically recover to its closed position cross-sectional profile or another cross-sectional profile, such as, one associated with a relaxed or non-stressed state. However, in the opened position shown in FIG. 8, the gingival side 460 of the closure portion 454 may still abut the shoulder 450 at the lingual side 420 of the bracket body 412, but the hinge pin 416 has forced the ligating latch 414, by virtue of recovery of its elastic deformation, to translate slightly in a gingival direction to hold the ligating latch 414 in the opened position. To move the ligating latch 414 from the opened position to the closed position, a clinician only needs to apply a sufficient force on the closure portion 454 of the ligating latch 414 to force the gingival side 460 over and beyond the shoulder 450 on the bracket body 412.

Consequently, the hinge pin 416 maintains the ligating latch member 414 in the closed position or the opened position. The ligating latch member 414 is easily moved by a tool or manually regardless of the limited visibility and space available for a clinician on the lingual side of bicuspid teeth. As such, the orthodontic bracket 410 is advantageous compared to conventional self-ligating brackets for at least the same reasons provided above for the other embodiments.

Figure 9:
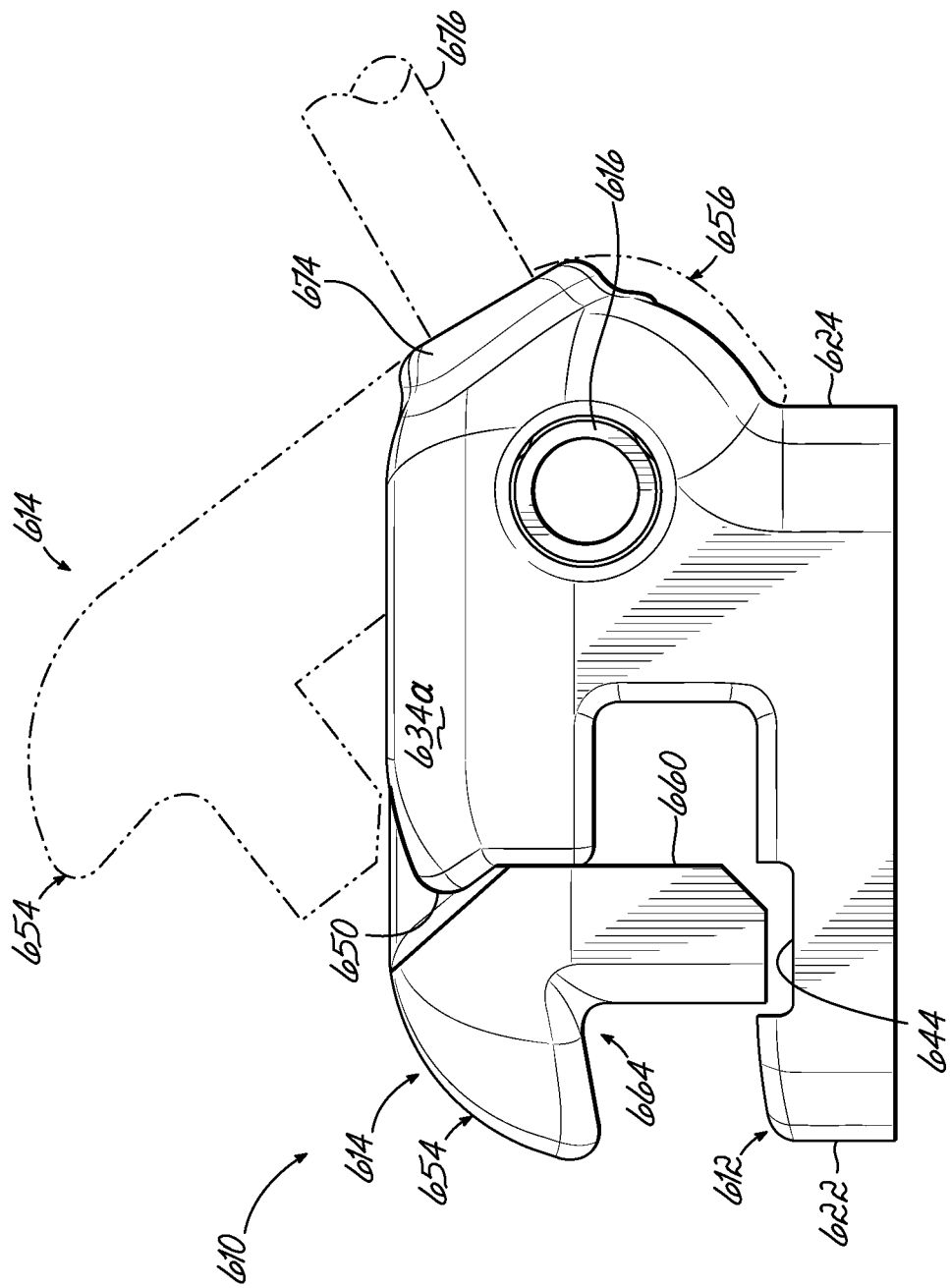
FIG. 9 is a side elevation view of a self-ligating orthodontic bracket in accordance with one embodiment of the invention, with a ligating latch shown in a closed position.

Another exemplary embodiment of a self-ligating orthodontic bracket 610 is illustrated in FIG. 9. This embodiment of the orthodontic bracket 610 is configured for use on the lingual side of molar teeth in the upper or lower jaw. The orthodontic bracket 610 includes many of the same elements and operational functionality as the embodiments disclosed above. However, by way of example only, the differences between the embodiment shown in FIG. 9 and above-identified embodiments are described in further detail below.

As shown in FIG. 9, the ligating latch 614 of this embodiment includes a closure portion 654 and a pivot portion 656, but no auxiliary portion. Similar to that disclosed above, the closure portion 654 includes an optional tie wing-like cavity 664 though it will be appreciated that the closure portion 654 may be plate-shaped in cross-section such that an occlusal side 622 of the closure portion 654 does not project beyond (in an occlusal direction) a latch slot 644 in the bracket body 612. In the embodiment shown, the auxiliary portion has been removed from the opposing side of the pivot portion 656. Thus, the ligating latch 614 does not effectively replace the tie wings on the bracket body 612 in this embodiment of the bracket 610.

The bracket body 612 in this embodiment has been modified to include a pair of circular-shaped standardized mounting depressions 674, as previously described with reference to the second embodiment (FIGS. 1 and 2). The mounting depressions 674 are formed along the gingival side 624 of the bracket body 612, and more particularly, at the first and second bracket body portions (body portion 634a shown in FIG. 9). The mounting depressions 674 are configured to receive auxiliary devices, such as, an auxiliary hook. As is well understood in the art, the auxiliary hook 676 may be used to couple ligatures or other orthodontic devices between two orthodontic brackets. The bracket body 612 is also formed with a wider mesial-distal dimension to correspond to the molar teeth, but this generally wide rectangular shape may be modified without departing from the scope of the invention.

The ligating latch 614 and the hinge pin 616 operate in an identical manner as embodiments described herein, advantageously retaining the ligating latch 614 in either the opened position or the closed position. In this regard, the gingival side 660 of the closure portion 654 of the ligating latch 614 may be forced by a tool or manually over the shoulder 650 in the bracket body 612, thereby deforming the hinge pin 616 within a pin aperture similar to the pin aperture 472. The orthodontic bracket 610 is advantageous compared to conventional self-ligating brackets for at least the same reasons provided above.

While the present invention has been illustrated by a description of various preferred embodiments and while these embodiments have been described in some detail, it is not the intention of the inventor to restrict or in any way limit the scope of the appended claims to such detail. Additional advantages and modifications will readily appear to those skilled in the art. The various features of the embodiments of the invention may be used alone or in any combinations depending on the needs and preferences of the user.

What is claimed is:

1. An orthodontic bracket for coupling an archwire with a tooth, the orthodontic bracket comprising:
    a bracket body configured to be mounted to the tooth and including an archwire slot having opposing first and second slot sides and a third slot side extending between the opposing first and second slot sides;
    a hinge pin including a first shaft portion operatively coupled with the bracket body and a second shaft portion; and
    a latch operatively coupled to the bracket body by the second shaft portion of the hinge pin for rotational movement about an axis of rotation defined by the hinge pin, the latch being movable between an opened position in which the archwire is insertable into the archwire slot and a closed position in which the latch retains the archwire in the archwire slot,
    wherein a cross-sectional profile of the first shaft portion and/or a cross-sectional profile of the second shaft portion of the hinge pin is configured to elastically deform to impart a spring bias to the latch that biases the latch in a direction intersecting a plane defining the third slot side, the cross-sectional profiles of each of the first shaft portion and the second shaft portion being taken perpendicular to the longitudinal axis of the respective shaft portion.

2. The orthodontic bracket of claim 1 wherein one of the first shaft portion and the second shaft portion of the hinge pin is configured to elastically deform from a first cross-sectional profile when the latch is in the closed position to a second cross-sectional profile when the latch is moved from the closed position, the spring bias opposing movement of the latch from the closed position, and the first cross-sectional profile and the second cross-sectional profile being different.

3. The orthodontic bracket of claim 2 wherein one of the first shaft portion and the second shaft portion of the hinge pin is configured to elastically deform from the second cross-sectional profile to a third cross-sectional profile when the latch is rotated toward the opened position.

4. The orthodontic bracket of claim 1 wherein the hinge pin is a hollow cylinder.

5. The orthodontic bracket of claim 1 wherein the bracket body includes a bore for receiving the first shaft portion and the latch includes an aperture for receiving the second shaft portion and at least one of the aperture and the bore has a non-symmetric cross-sectional profile, the non-symmetric cross-sectional profile being in the same plane as the corresponding shaft cross-sectional profile and with the non-symmetry being determined across a plane that includes the axis of rotation.

6. The orthodontic bracket of claim 1 wherein the bracket body includes a bore for receiving the first shaft portion and the latch includes an aperture for receiving the second shaft portion, the bore including a bore cross-sectional profile and the aperture including an aperture cross-sectional profile, each of the cross-sectional profiles being in the same plane as the corresponding shaft cross-sectional profile, one of the bore cross-sectional profile and the aperture cross-sectional profile being substantially non-congruent relative to the corresponding cross-sectional profile of the first shaft portion or second shaft portion, the hinge pin being configured to move relative to the bore or the aperture and elastically deform toward at least a portion of the substantially non-congruent cross-sectional profile.

7. The orthodontic bracket of claim 6 wherein the aperture cross-sectional profile is substantially non-congruent relative to the cross-sectional profile of the second shaft portion and includes a central portion and a first narrowed end, the second shaft portion being located in the central portion when the latch is in the closed position and elastically deforms into the first narrowed end when the latch is moved from the closed position.

8. The orthodontic bracket of claim 7 wherein the central portion of the aperture cross-sectional profile is sized to elastically deform the hinge pin in the closed position.

9. The orthodontic bracket of claim 6 wherein the substantially non-congruent cross-sectional profile includes a first narrowed end that is contiguous with a central portion and wherein one of the first shaft portion and the second shaft portion is located in the central portion when the latch is in the closed position and elastically deforms into the first narrowed end when the latch is moved from the closed position.

10. The orthodontic bracket of claim 9 wherein the substantially non-congruent cross-sectional profile includes a second narrowed end that is contiguous with the central portion and one of the first shaft portion and the second shaft portion elastically deforms into the second narrowed end when the latch is moved toward the opened position.

11. The orthodontic bracket of claim 10 wherein the latch includes an outer periphery including a cam surface configured to contact the bracket body and move the latch in a non-collinear direction relative to the axis of rotation when the latch is rotated about the axis of rotation from the closed position to the opened position.

12. The orthodontic bracket of claim 11 wherein the cam surface is configured to contact the bracket body to hold the latch in the opened position.

13. The orthodontic bracket of claim 1 wherein the bracket body includes a shoulder engaged with the latch when the latch is in the closed position, so as to inhibit movement of the latch about the axis of rotation from the closed position toward the opened position, the spring bias of the hinge pin opposing movement of the latch away from the shoulder.

14. The orthodontic bracket of claim 1 wherein the side of the latch that closes off the archwire slot when the latch is in the closed position is movable in a direction away from the axis of rotation when the latch is moved toward the opened position.

15. The orthodontic bracket of claim 1 wherein the hinge pin is compressed when the latch is in the closed position.

16. The orthodontic bracket of claim 1 wherein the bracket body includes a shaped projection for insertion into a corresponding receptacle formed on a pad that is configured to be secured to a tooth.

17. The orthodontic bracket of claim 1 wherein elastic deformation includes a change in at least one dimension of the cross-sectional profile of one of the first shaft portion and the second shaft portion in a direction perpendicular to the longitudinal axis of the hinge pin.

18. The orthodontic bracket of claim 17 wherein the bracket body includes a bore for receiving the first shaft portion and the latch includes an aperture for receiving the second shaft portion, wherein the change in the at least one dimension of the cross-sectional profile is to conform the at least one dimension to a dimension on the corresponding one of the bore or the aperture.

19. The orthodontic bracket of claim 17 wherein the cross-sectional profile of the hinge pin is configured to elastically deform at the location of contact between the hinge pin and the latch or the hinge pin and the body.

20. An orthodontic bracket for coupling an archwire with a tooth, the orthodontic bracket comprising:
    a bracket body including an archwire slot having opposing first and second slot sides and a third slot side extending between the opposing first and second slot sides;
    a pin; and
    a latch including a pin aperture to receive the pin and being operatively coupled to the bracket body by the pin for rotational movement between an opened position and a closed position, the latch including a closure portion having a surface that opposes the third slot side when the latch is in the closed position,
    wherein when the latch is in the closed position, the pin is elastically deformed so as to impart a spring bias to the latch to maintain the latch in the closed position.

21. The orthodontic bracket of claim 20 wherein the latch is L-shaped.

22. The orthodontic bracket of claim 20 wherein when the bracket body is mounted to the tooth, the archwire slot opens in the occlusal direction and the closure portion is biased in the gingival direction when the latch is in the closed position.

23. The orthodontic bracket of claim 20 wherein to move the latch to the opened position from the closed position, the closure portion is moved in a direction away from the longitudinal axis of the pin.

24. The orthodontic bracket of claim 20 wherein when the latch is in the opened position, the pin is in a non-stressed state.

25. An orthodontic bracket for coupling an archwire with a tooth, the orthodontic bracket comprising:
    a bracket body including an archwire slot having opposing first and second slot sides and a third slot side extending between the opposing first and second slot sides, the third slot side being configured to face in an occlusal direction when the bracket body is attached to the tooth;
    a pin; and
    a latch being operatively coupled to the bracket body by the pin for rotational movement between an opened position and a closed position, the latch having a closure portion facing the third slot side when the latch is in the closed position, the third slot side being between the closure portion and the pin, the pin being elastically deformed when the latch is moved from the closed position to the opened position.

26. The orthodontic bracket of claim 25 wherein the bracket body includes a shoulder engagable with the latch when the latch is in the closed position so as to inhibit movement of the latch about the axis of rotation from the closed position toward the opened position, wherein the closure portion is moved away from the third slot side to clear the shoulder to move the latch toward the opened position.

27. The orthodontic bracket of claim 25 wherein the bracket body further includes a side that is configured to be coupled to a surface of the tooth, the side being substantially perpendicular to the third slot side.

28. The orthodontic bracket of claim 25 wherein the pin is elastically deformed so as to impart a spring bias to the latch to maintain the latch in the closed position.

29. The orthodontic bracket of claim 28 wherein when the latch is in the opened position, the pin is in a non-stressed state.

30. The orthodontic bracket of claim 25 wherein to move the latch to the opened position from the closed position, the closure portion is moved in a direction away from the longitudinal axis of the pin.

* * * * *